United States Patent [19]

Frech et al.

[11] 4,256,880

[45] Mar. 17, 1981

[54] CONTINUOUS MORPHOLINE PROCESS

[75] Inventors: Kenneth J. Frech; Lawson G. Wideman, both of Tallmadge, Ohio

[73] Assignee: The Goodyear Tire & Rubber Company, Akron, Ohio

[21] Appl. No.: 58,043

[22] Filed: Jul. 16, 1979

[51] Int. Cl.³ .......................................... C07D 295/02
[52] U.S. Cl. .................................................... 544/106
[58] Field of Search ........................................ 544/106

[56] References Cited

U.S. PATENT DOCUMENTS

| | | | |
|---|---|---|---|
| 2,529,923 | 11/1950 | Dickey et al. | 260/584 B |
| 3,151,112 | 9/1964 | Moss | 544/106 |
| 3,709,881 | 1/1973 | Warner | 544/178 |

*Primary Examiner*—Henry R. Jiles
*Assistant Examiner*—R. W. Ramsuer
*Attorney, Agent, or Firm*—J. Y. Clowney

[57] ABSTRACT

A process for preparing morpholine from diethyleneglycol and an aqueous solution of ammonia in a continuous manner using a modified Raney nickel catalysts without the use of any hydrogen is disclosed.

7 Claims, No Drawings

CONTINUOUS MORPHOLINE PROCESS

TECHNICAL FIELD

This invention relates to a relatively low temperature low pressure process for the preparation of morpholine from diethyleneglycol and ammonia or an aqueous solution of ammonia in a continuous reactor over a fixed bed catalyst of modified Raney nickel without the use of any hydrogen. Mixtures of diethyleneglycol and diglycolamine may also be used as a reactant with ammonia or ammonium hydroxide to prepare the morpholine.

BACKGROUND ART

The preparation of morpholine from diethylene glycol and ammonia is not new, but all of the known prior processes for the manufacture of morpholine from diethyleneglycol and ammonia require the use of large amounts of hydrogen or ammonia, which results in the use of high pressure equipment and the employment of stringent operating conditions.

For instance, in U.S. Pat. No. 3,155,657, there is described a process for the preparation of morpholine from diethylene glycol, anhydrous ammonia and hydrogen at pressures up to 500 atmospheres and temperatures up to 240° C. using a catalyst of about 0.2 to 5 percent by weight of ruthenium on alumina.

In U.S. Pat. No. 3,151,112, there is described a process for the preparation of morpholine from diethylene glycol and anhydrous ammonia and hydrogen at temperatures of 150° C. to 400° C. and at pressures between 30 and 400 atmospheres where the partial pressure of the hydrogen is at least 10 atmospheres using catalysts from the group of copper, nickel, chromium, cobalt, magnesium, molybdenum, palladium, platinum, rodium, their oxides or mixtures thereof.

Japanese patent application No. 039937 published as No. 7132189 discloses the preparation of morpholine from diethylene glycol, ammonia and hydrogen at 25 atmospheres using a catalyst prepared by boiling a 50/50 nickel/aluminum alloy in water for 4 hours.

In U.S. Pat. No. 3,347,926 there is disclosed a process for producing aliphatic amines by ammonolysis by reacting a hydroxy containing compound, such as primary and secondary alcohols with ammonia, primary and secondary amines in the presence of Raney nickel catalyst containing some chromium at temperatures from 150° C. to 275° C.

In U.S. Pat. No. 3,709,881 there is disclosed the preparation of N-alkyl morpholines from diethylene glycol and an alkyl, dialkyl or trialkyl amine in the presence of a hydrogenation catalyst preferably in the presence of hydrogen, at elevated temperatures and pressures in the presence of water.

In the Russian Journal, Zh. Vses. Khim. Obshchest, 14 (5); pp. 589–590, Dobrovolski et al disclose the reaction of diethylene glycol/ammonia/hydrogen at mole ratios of 1/10/5 in the gas phase over a nickel based catalyst.

In U.S. Pat. No. 2,412,209 there is disclosed a process for the preparation of aliphatic amines by the condensation of ammonia with dihydric alcohols by saturating the glycol with ammonia in the presence of a hydrogenation catalyst, such as Raney nickel, copper chromite, copper nickel chromite, iron, etc.

Japanese patent application No. 013882 published as 7131863 discloses the preparation of morpholine from diethylene glycol and a gaseous mixture of ammonia and hydrogen and steam at about 8 moles of hydrogen per mole of ethylene glycol at about 190° C. and using a nickel catalyst.

Japanese patent application No. 103791 published as No. 7241908 discloses the preparation of morpholine by reacting ethylene glycol with ammonia and hydrogen utilizing a catalyst which is a mixture of nickel, copper and molybdenum oxide.

Japanese patent application No. 039936 published as No. 7132188 discloses the preparation of morpholine by reacting ethylene glycol, ammonia in the presence of hydrogen at about 26 atmospheres at 240° C. utilizing a Raney nickel alloy.

The present invention has the advantage over these prior processes in that no hydrogen whatever is required in the process of this invention. Therefore, the use of the high pressure of the prior art is eliminated. Also, one of the advantages of the process of this invention is that the ammonia can be utilized in the form of ammonium hydroxide.

The present invention has other advantages over these prior art processes in that it employs temperatures and pressures much lower than the prior art methods. The invention also provides greater selectivity to morpholine than the prior art methods. The catalyst which is employed in the present invention is much easier to regenerate in a continuous reactor than in the prior art batch methods.

DISCLOSURE OF THE INVENTION

According to the invention, morpholine is prepared in a continuous reaction by reacting diethyleneglycol and an aqueous solution of ammonia using as a catalyst a particular granular form of modified Raney nickel catalyst which has been prepared by reacting a nickel-aluminum alloy with an alkaline earth or an alkali metal hydroxide in which the molar ratio of ammonia to diethyleneglycol ranges from about 1.2/1 to about 10/1, and in which the molar ratio of water to diethylene glycol ranges from about 2.35/1 to about 12.46/1.

In another embodiment of the invention, morpholine is prepared by reacting a mixture of diethyleneglycol and diglycolamine continuously with an aqueous solution of ammonia using the same catalyst and ammonia/ethylene glycol diglycolamine molar ratio and the same water to diethyleneglycol ratio.

DETAILED DESCRIPTION OF THE INVENTION

As has been indicated, an aqueous solution of ammonia and diethyleneglycol (DEG) or a mixture of diglycolamine DGA) and DEG are charged continuously in intimate contact with the catalyst system.

The rate at which the mixture of aqueous ammonia and DGA and DEG or DEG are charged to the reactor may vary widely. For instance, the volume of the feed to the volume of the catalyst per hour, known as liquid hour space velocity (LHSV), for the mixture of aqueous ammonia and DEG or mixtures of DEG and DGA may vary from about 0.5 to about 15. A more preferred LHSV ranges from about 1 to about 10, and a range of LHSV may be 1.5 to 8 is most preferred.

The temperature maintained when the reaction takes place can also be varied quite widely from about 160° C. to about 260° C. with a more preferred reaction temperature of about 180° C. to about 220° C. It has been determined that reaction temperatures in excess of 260° C. are not at all desired.

The molar ratio of the water to diethylene glycol can range from about 2.35/1 to about 12.46/1. A more preferred mole ratio is about 2.4/1 to about 8.0/1.

It is important to use as a minimum a molar ratio of water to diethylene glycol to about 2.4/1. It has been determined that when too little water is employed in the process of this invention both the conversion of the diethylene glycol and the selectivity to morpholine drop off.

The molar ratio of ammonia to diethylene glycol may range from about 1.2/1 to about 10/1. However, a molar ratio of about 1.2/1 to about 5/1 is preferred.

The concentration of ammonia in the water will, of course, depend on the ratio of water to diethylene glycol chosen. One skilled in the art would realize that if one chooses to run with a low ratio of water to DEG, a high ratio of ammonia to water would be required to obtain at least one molar equivalent of ammonia per mole of diethylene glycol. On the other hand, if the ratio of water to DEG is set at about 50 percent, then the ammonia to water ratio would be represented fairly well with a 30 percent aqueous ammonia solution. A 30 percent aqueous ammonia solution is usually commercially available as ammonium hydroxide. However, a 30% aqueous ammonium hydroxide solution can be further fortified with anhydrous ammonia under pressure to form a 50 to 90 percent aqueous ammonia solution. If such a material is used, extremely undesirable high reaction pressures will result.

The reaction pressure which has been found to be most advantageous may range from about 100 psig (7.031 kgs/sq cm) to about 2000 psig (1406.2 kg/sq cm) with about 200 psig (14.06 kgs/sq cm) to about 1000 psig (70.3 kgs/sq cm) being most preferred. The most optimum pressure in which to conduct the invention ranges from about 300 psig (21.09 kgs/sq cm) to about 600 psig (42.186 kgs/sq cm).

When in the practice of the invention there is recycling of diglycolamine and unconverted diethyleneglycol, an additional diethyleneglycol is added to this recycle for further reaction with the ammonia to form morpholine. The ratio of diglycolamine to diethyleneglycol in the feed can vary widely. However, since it is desirable to produce a maximum amount of morpholine from diethylene glycol at a given set of operating conditions, the ratio of diglycolamine and diethyleneglycol can be optimized to give the maximum amount of morpholine from the starting material, diethyleneglycol. This ratio is usually governed by the amount of diglycolamine produced in the continuous operation of the invention. For instance, if for every 1000 kilograms of diethyleneglycol and ammonia were fed to the reactor and 200 kilograms are reacted, the amount of diglycolamine produced would be about 78 kilograms along with about 55 kilograms of morpholine and about 40 kilograms of unreacted diethyleneglycol. Thus, under these operating conditions, one would want to adjust the ratio of diglycolamine to diethyleneglycol at a ratio of about 1 kilogram of diglycolamine to about 2.6 kilograms of diethyleneglycol in the feed. Thus, in this hypothetical example, the additional amount of diethyleneglycol needed to be added to the recycle would be 164 kilograms. By adjusting the percentage of diglycolamine in the total feed of a mixture of diethyleneglycol and diglycolamine, one can tend to prevent the formation of an excess of diglycolamine and maximize the conversion of diethyleneglycol and ammonia or ammonia hydroxide to the desired produced morpholine.

Thus, about 20% to about 65% by weight of the diethyleneglycol can be replaced by diglycolamine in the method of this invention.

The use of hydrogen is not required in this invention. In fact, it has been found that any added hydrogen is usually detrimental. Hydrogen seems to cause the selectivity to morpholine to decrease.

Preparation of the Catalyst

The catalyst employed in the process of the invention is prepared by reacting a nickel-aluminum alloy with alkaline earth or an alkali metal hydroxide, particularly sodium or potassium hydroxide. The alloy may vary in composition from bout 30 percent by weight of nickel up to about 70 percent by weight of nickel, the remainder being aluminum. The alloy should be of a size to give maximum surface area to the finished catalyst and yet have structural integrity.

It has been found that the optimum particle size of catalyst will depend on the size and diameter of the reactor employed. The ratio of reactor diameter to nominal catalyst diameter ($D/D'$) may vary broadly and range from about 4 to 1 to about 20 to 1 or higher; one skilled in the art would realize that pressure-drop or plugging problems would result when the particle size becomes too small. Excellent results can be obtained if the $D/D'$ ratio is maintained at about 6 to 1, to about 10 to 1.

The granular particles of alloy are added slowly to a boiling solution of alkaline earth or alkali metal hydroxide where some of the aluminum in the alloy reacts to form the metal aluminate, while hydrogen is evolved. After the evolution of hydrogen ceases, the catalyst is digested at 90° to 100° C. for one-half hour. The catalyst is then washed with water to free it of the alkaline earth or alkali metal salts such as potassium aluminate and potassium hydroxide.

It is important that air is not entrained onto the catalyst during the catalyst wash with water, and that the catalyst is always covered with water or an aqueous solution, as a loss in catalyst activity will result if air is brought into intimate contact with the system.

It has been observed that when only DEG is used as the feedstock and no DGA is recycled, a greater ultimate yield of morpholine is obtained when potassium hydroxide is used to prepare the catalyst. In this event potassium hydroxide is much preferred.

The invention is further exemplified by reference to the following examples which are intended to be representative rather than restrictive of the scope of the invention.

In these examples, DEG means diethyleneglycol; Morph is morpholine and DGA means diglycolamine.

In these examples, Table 1 shows the effect of varying the molar ratio of the ammonia to diethyleneglycol; Table 2 shows the effect of varying the reaction pressure; Table 3 shows the effect of varying the reaction temperature; Table 4 shows the effect of varying the flow rate; Table 5 shows the effect of varying the metal hydroxide employed to prepare the catalyst with diethyleneglycol as a feed; Table 6 shows the effect of varying the metal hydroxide in preparation of the catalyst in which the feed is a 50 percent by weight mixture of diglycolamine and diethyleneglycol.

In Tables 1, 2, 3 and 4, column 1 is the run number, column 2 is the feed, column 3 is the time that the continuous process was on stream, column 4 is the molar ratio of ammonia to diethyleneglycol, column 5 is the flow rate in cc's per minute, column 6 is the liquid hour space velocity, column 7 is the reaction pressure in pounds per square inch gauge; column 8 is the reaction temperature; column 9 is the diethylene glycol conversion in percent diethyleneglycol consumed; column 10 is the selectivity to morpholine, column 11 is the selectivity to diglycolamine.

In Table 5 column 1 is the run number, column 2 is the time the reaction was continuously on stream, column 3 is the metal hydroxide employed in the preparation of the catalyst. The remaining columns are the same as the previous tables.

In Table 6 the columns are the same as in Table 5 except that column 4 is the molar ratio of ammonia to the mixture of diethyleneglycol and diglycolamine and column 9 is the conversion of mixture of diglycolamine and diethyleneglycol, and column 10 is the selectivity to morpholine.

In the following examples each run was conducted in an up-flow stainless steel tubular reactor having about 60 cubic centimeters volume which was loaded with 45 cc of crushed modified Raney nickel catalyst that had been prepared from 80 grams (g) of nickel aluminum alloy, 112 g of potassium hydroxide and 800 ml of water in accordance with the previous teachings in this application. The reactor was slowly heated to the desired reaction temperature with an up-flow of diethyleneglycol (mixtures of diethyleneglycol and diglycolamine) and ammonium hydroxide (30% ammonia) at the desired ammonia/diethyleneglycol molar ratios. The on-stream time was started when the temperature of the system reached the desired reaction temperature. At the end of one hour on stream, a sample was taken and subjected to chromatographic analysis with a weighted internal standard.

TABLE 1

| Run No. | Feed | On-Stream time (hr) | $H_2O$/DEG (molar) | $NH_3$/DEG (Molar) | Flow Rate (cc/min) | LHSV | React Pres. psig | React temp. (°C.) | DEG Conv (%) | Morph Sel (%) | DGA Sel (%) |
|---|---|---|---|---|---|---|---|---|---|---|---|
| 1 | DEG | 1 | 3.1 | 1.3 | 2.0 | 2.67 | 400 | 200 | 46.1 | 41.2 | 40.1 |
| 2 | DEG | 1 | 2.8 | 1.2 | 2.0 | 2.67 | 600 | 200 | 65.9 | 49.6 | 22.8 |
| 3 | DEG | 1 | 4.4 | 1.8 | 2.0 | 2.67 | 400 | 200 | 67.9 | 52.0 | 17.5 |
| 4 | DEG | 1 | 4.4 | 1.8 | 2.0 | 2.67 | 600 | 200 | 65.5 | 51.8 | 24.9 |
| 5 | DEG | 1 | 5.2 | 2.2 | 2.0 | 2.67 | 400 | 200 | 53.5 | 45.8 | 32.9 |
| 6 | DEG | 1 | 5.2 | 2.2 | 2.0 | 2.67 | 600 | 200 | 66.8 | 51.8 | 24.3 |

TABLE 2

| Run No. | Feed | On-Stream time (hr) | $H_2O$/DEG (Molar) | $NH_3$/DEG (molar) | Flow Rate (cc/min) | LHSV | React pres. psig | React temp. (°C.) | DEG Conv (%) | Morph Sel (%) | DGA Sel (%) |
|---|---|---|---|---|---|---|---|---|---|---|---|
| 1 | DEG | 1 | 4.4 | 1.8 | 2.0 | 2.67 | 200 | 220 | 79.5 | 30.1 | 2.1 |
| 2 | DEG | 1 | 2.8 | 1.2 | 2.0 | 2.67 | 300 | 220 | 73.2 | 42.4 | 6.9 |
| 3 | DEG | 1 | 4.4 | 1.8 | 2.0 | 2.67 | 400 | 220 | 62.4 | 51.4 | 22.8 |
| 4 | DEG | 1 | 4.4 | 1.8 | 2.0 | 2.67 | 600 | 220 | 64.3 | 51.2 | 25.0 |
| 5 | DEG | 1 | 5.2 | 2.2 | 2.0 | 2.67 | 700 | 220 | 82.8 | 42.6 | 6.9 |
| 6 | DEG | 1 | 5.2 | 2.2 | 2.0 | 2.67 | 800 | 220 | 81.4 | 35.2 | 6.7 |

TABLE 3

| Run No. | Feed | On-Stream time (hr) | $H_2O$/DEG (molar) | $NH_3$/DEG (molar) | Flow Rate (cc/min) | LHSV | React pres. psig | React temp. (°C.) | DEG Conv (%) | Morph Sel (%) | DGA Sel (%) |
|---|---|---|---|---|---|---|---|---|---|---|---|
| 1 | DEG | 1 | 0 | 0 | 1.8 | 2.0 | 400 | 240 | exothermed to 400° C. | | |
| 2 | DEG | 1 | 2.4 | ½ | 1.8 | 2.67 | 400 | 260 | 93.3 | 11.3 | 1.0 |
| 3 | DEG | 1 | 2.4 | 1 | 1.8 | 2.67 | 400 | 240 | 75.9 | 40.8 | 7.1 |
| 4 | DEG | 1 | 2.4 | 1 | 1.8 | 2.67 | 400 | 220 | 62.4 | 51.4 | 22.8 |
| 5 | DEG | 1 | 2.4 | 1 | 1.8 | 2.67 | 400 | 210 | 59.5 | 45.3 | 24.4 |
| 6 | DEG | 1 | 2.4 | 1 | 1.8 | 2.67 | 400 | 200 | 46.1 | 41.2 | 40.1 |
| 7 | DEG | 1 | 7.8 | 4.0 | 1.8 | 5.33 | 400 | 210 | 61.9 | 40.8 | 16.7 |
| 8 | DEG | 1 | 7.8 | 4.0 | 1.8 | 5.33 | 400 | 220 | 54.4 | 46.4 | 20.1 |
| 9 | DEG | 1 | 7.8 | 4.0 | 1.8 | 5.33 | 400 | 240 | 66.1 | 39.0 | 9.9 |

TABLE 4

| Run No. | Feed | On-Stream time (hr) | $H_2O$/DEG (molar) | $NH_3$/DEG (molar) | Flow Rate (cc/min) | LHSV | React pres. psig | React temp. (°C.) | DEG Conv. (%) | Morph Sel (%) | DGA Sel (%) |
|---|---|---|---|---|---|---|---|---|---|---|---|
| 1 | DEG | 1 | 4.4 | 1.8 | 1.5 | 2.0 | 400 | 220 | 74.0 | 35.5 | 8.9 |
| 2 | DEG | 1 | 4.4 | 1.8 | 2.0 | 2.67 | 400 | 220 | 62.4 | 51.4 | 22.8 |
| 3 | DEG | 1 | 4.4 | 1.8 | 3.0 | 4.00 | 400 | 220 | 67.3 | 44.0 | 10.2 |
| 4 | DEG | 1 | 4.4 | 1.8 | 3.53 | 4.72 | 400 | 220 | 58.3 | 49.6 | 20.4 |
| 5 | DEG | 1 | 4.4 | 1.8 | 4.00 | 5.37 | 400 | 220 | 54.4 | 46.4 | 20.1 |

TABLE 5

| Run No. | On Stream time (hr) | Metal hydroxide | NH₃/DEG (molar) | Flow rate (cc/min) | H₂O/DEG (molar) | LHSV | React pres. psig | React temp. (°C) | Conv DEG (%) | Sel Morph (%) | Sel DGA (%) |
|---|---|---|---|---|---|---|---|---|---|---|---|
| 1 | 1 | Ba(OH)₂ | 1.8 | 2.2 | 4.4 | 2.98 | 600 | 200 | 73.9 | 53.6 | 10.7 |
| 2 | 1 | Ba(OH)₂ | 1.8 | 2.2 | 4.4 | 2.98 | 400 | 200 | 40.5 | 35.9 | 37.0 |
| 3 | 1 | LiOH | 1.8 | 2.2 | 4.4 | 2.98 | 600 | 200 | 40.5 | 35.7 | 42.8 |
| 4 | 1 | LiOH | 1.8 | 2.2 | 4.4 | 2.98 | 400 | 200 | 25.7 | 25.7 | 47.2 |
| 5 | 1 | KOH | 1.8 | 2.2 | 4.4 | 2.98 | 400 | 200 | 48.2 | 78.2 | 21.3 |

Ba(OH)₂ — barium hydroxide
LiOH — lithium hydroxide
KOH — potassium hydroxide

TABLE 6

| Run No | On-Stream time (hr) | Metal hydroxide | H₂O/DEG (molar) | NH₃/DEG (molar) | Flow Rate (cc/min) | LHSV | React pres. (psig) | React temp. (°C) | DGA + DEG Conv. (%) | Morph Sel (%) |
|---|---|---|---|---|---|---|---|---|---|---|
| 1 | 1 | NaOH | 4.4 | 1.8 | 2.2 | 2.98 | 400 | 200 | 43.0 | 88.4 |
| 2 | 1 | KOH | 4.4 | 1.8 | 2.2 | 2.98 | 400 | 200 | 45.0 | 86.4 |
| 3 | 1 | Ba(OH)₂ | 4.4 | 1.8 | 2.2 | 2.98 | 400 | 200 | 23.1 | 95.0 |
| 4 | 1 | LiOH | 4.4 | 1.8 | 2.2 | 2.98 | 400 | 200 | 16.9 | 95.0 |
| 5 | 1 | Ba(OH)₂ | 4.4 | 1.8 | 2.2 | 2.98 | 600 | 200 | 21.5 | 95.0 |

NaOH — sodium hydroxide
KOH — potassium hydroxide
Ba(OH)₂ — barium hydroxide
LiOH — lithium hydroxide

COMPARATIVE EXAMPLE

In this example of a batch process, a 1 liter stainless steel reactor was flushed with nitrogen and charged with 75.0 g of 30 percent ammonium hydroxide (1.32 moles NH₃), followed by a suspension of 12.5 g of the modified T-1 Raney nickel in 100.0 g (0.94 mole) of diethyleneglycol. The reactor gauge pressure was zero at room temperature. Heat was then applied and the temperature was raised to 200° C. as quickly as possible, about 45 minutes, and the temperature was maintained at 200° C. with stirring. The pressure was 31.6 kg/cm² gauge. After four hours, the reactor was cooled to room temperature with internal cooling coils. The contents of the reactor were removed from the nickel catalyst via an internal dip-leg. Gas chromatographic analysis (with a weighted internal standard added) revealed:

89.7% diethyleneglycol conversion
59.0% morpholine selectivity
8.3% diglycolamine selectivity This results in an ultimate yield of 52.9% of morpholine. The reaction mixture was distilled to yield 45.0 g of 99.8 percent pure morpholine, as shown by gas chromatographic, infrared and nuclear magnetic resonance spectroscopy analyses.

Industrial Applicability

Thus, it can be seen that the continuous feed of either diethyleneglycol or mixtures of diethyleneglycol and diglycolamine with catalyst that have been treated with alkaline earth and alkaline metal hydroxides give excellent results when ammonia is employed to form morpholine without the use of any added hydrogen. Morpholine is a useful chemical in the treatment of boiler water and it is also useful as a chemical in rubber compounding.

While certain representative embodiments and details have been shown for the purpose of illustrating the invention, it will be apparent to those skilled in this art that various changes and modifications may be made therein without departing from the spirit or scope of the invention.

We claim:

1. In a method for the preparation of morpholine by reacting diethyleneglycol and ammonia, the improvement characterized by using as a catalyst, a particular granular form of modified Raney nickel catalyst which has been prepared by reacting a nickel aluminum alloy with an alkaline earth or an alkali metal hydroxide, and in which the ammonia employed is an aqueous solution of ammonia, and in which the molar ratio of ammonia to diethyleneglycol ranges from about 1.2/1 to about 10/1, and the molar ratio of water to diethyleneglycol ranges from about 2.35/1 to about 12.46/1, said reaction being conducted in the absence of hydrogen, and said reaction being conducted as a continuous reaction.

2. The method according to claim 1 in which the molar ratio of ammonia to diethylene glycol ranges from about 1.2 moles to about 5.0 moles of ammonia per mole of diethylene glycol and in which the molar ratio of water to diethylene glycol ranges from about 2.4/1 to about 8.0/1.

3. The method according to claim 2 in which the ratio of ammonia to diethylene glycol ranges from about 1.2 moles to about 4.0 moles of ammonia per mole of diethylene glycol.

4. The method according to claim 1 in which the temperature of reaction does not exceed 260° C.

5. The method according to claim 1 in which about 20 percent to about 65 percent by weight of the diethyleneglycol is replaced by diglycolamine.

6. The method according to claim 5 in which the ratio of ammonia to the mixture of diethyleneglycol and diglycolamine ranges from about 1.2 moles to about 5.0 moles of ammonia per mole of the said mixture.

7. The method according to claim 5 in which the temperature of reaction does not exceed 260° C.

* * * * *